United States Patent
Ellis

(10) Patent No.: US 9,468,423 B2
(45) Date of Patent: Oct. 18, 2016

(54) SAFETY SHIELD FOR FLUID SPECIMEN CONTAINER

(75) Inventor: Robert G. Ellis, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 63 days.

(21) Appl. No.: 13/347,138

(22) Filed: Jan. 10, 2012

(65) Prior Publication Data

US 2013/0175266 A1  Jul. 11, 2013

(51) Int. Cl.
 *A61B 10/00*  (2006.01)
 *B01L 3/00*  (2006.01)

(52) U.S. Cl.
 CPC .............. *A61B 10/007* (2013.01); *B01L 3/502* (2013.01); *B01L 3/5635* (2013.01); *A61B 10/0096* (2013.01); *A61B 2090/0801* (2016.02); *B01L 2200/026* (2013.01)

(58) Field of Classification Search
 CPC ........... A61B 10/0045; A61B 10/007; A61M 2202/0014; A61M 39/1011; A61M 2039/1016; A61M 2039/1066; A61J 1/1412; A61J 1/1425; A61J 1/1481; A61J 1/2048; A61J 1/2051; A61J 1/2055; A61J 1/2065
 See application file for complete search history.

(56) References Cited

U.S. PATENT DOCUMENTS

| | | |
|---|---|---|
| 2,639,806 A | 5/1953 | Recht |
| 3,392,859 A | 7/1968 | Fischer |
| 3,433,712 A | 3/1969 | Gerarde |
| 3,522,734 A | 8/1970 | Curby |
| 3,579,306 A | 5/1971 | Crane |
| 3,620,408 A | 11/1971 | Holbrook et al. |
| 3,655,096 A | 4/1972 | Easter |
| 3,904,482 A | 9/1975 | Mehl |
| 4,064,760 A | 12/1977 | Benjamin |
| 4,116,066 A | 9/1978 | Mehl et al. |
| 4,186,840 A | 2/1980 | Percarpio |
| 4,210,623 A | 7/1980 | Breno et al. |
| 4,244,478 A | 1/1981 | Handman |
| 4,300,404 A | 11/1981 | Mehl et al. |
| 4,559,649 A | 12/1985 | Burnett |
| 4,852,560 A | 8/1989 | Hermann, Jr. et al. |
| 4,886,071 A | 12/1989 | Mehl et al. |
| 4,927,605 A | 5/1990 | Dorn et al. |
| 4,934,547 A | 6/1990 | Mayes et al. |
| 5,254,312 A | 10/1993 | Staebler et al. |
| 5,286,453 A | 2/1994 | Pope |
| 5,312,009 A | 5/1994 | Ratajczak et al. |

(Continued)

FOREIGN PATENT DOCUMENTS

| | | |
|---|---|---|
| EP | 0787987 A2 | 8/1997 |
| GB | 2060583 A | 5/1981 |

(Continued)

*Primary Examiner* — Philip R Wiest
*Assistant Examiner* — Sara Sass
(74) *Attorney, Agent, or Firm* — The Webb Law Firm

(57) ABSTRACT

A container assembly including a shield disposed at least partially within a receiving cavity of a receptacle of a lid is disclosed. The shield provides a physical barrier that at least partially covers and blocks an entrance to the receiving cavity to prevent a patient and/or healthcare worker from needle stick injuries. In one embodiment, the shield is adapted to receive a stopper of a collection tube, and the shield is transitionable between a locked position in which the shield is restrained within an open end of the receptacle, and an unlocked position in which the shield is movable within the receiving cavity of the receptacle.

23 Claims, 12 Drawing Sheets

(56) References Cited

U.S. PATENT DOCUMENTS

| | | |
|---|---|---|
| 5,344,417 A | 9/1994 | Wadsworth, Jr. |
| 5,344,666 A | 9/1994 | Levine |
| 5,380,314 A | 1/1995 | Herweck et al. |
| 5,429,803 A | 7/1995 | Guirguis |
| 5,512,042 A | 4/1996 | Montoya et al. |
| 5,714,125 A | 2/1998 | Sagstetter |
| 5,743,861 A | 4/1998 | Columbus et al. |
| 6,054,326 A | 4/2000 | Dubus |
| 6,071,095 A | 6/2000 | Verkaart |
| 6,203,503 B1 | 3/2001 | Kelly et al. |
| 6,235,010 B1 | 5/2001 | Wilkinson et al. |
| 6,247,592 B1 | 6/2001 | Racicot et al. |
| 6,255,101 B1 | 7/2001 | Rousseau et al. |
| 6,342,183 B1 | 1/2002 | Lappe et al. |
| 6,354,603 B1 | 3/2002 | Villette |
| 6,382,441 B1 | 5/2002 | Carano |
| 6,391,014 B1 | 5/2002 | Silverman |
| 6,571,837 B2 | 6/2003 | Jansen et al. |
| 6,599,273 B1 | 7/2003 | Lopez |
| 6,601,721 B2 | 8/2003 | Jansen et al. |
| 6,776,059 B2 | 8/2004 | Kunimune et al. |
| 6,899,850 B2 | 5/2005 | Haywood et al. |
| 2002/0079284 A1 | 6/2002 | Carano |
| 2003/0064526 A1* | 4/2003 | Niedbala ............ A61B 10/0045 436/165 |
| 2004/0108293 A1 | 6/2004 | Brockwell |
| 2004/0267159 A1* | 12/2004 | Yong et al. ................... 600/575 |
| 2005/0010189 A1* | 1/2005 | Toomey ............... A61B 5/1411 604/403 |
| 2009/0069783 A1* | 3/2009 | Ellstrom ............ A61M 39/1011 604/415 |
| 2009/0209044 A1* | 8/2009 | Gallagher et al. ............ 436/174 |
| 2010/0137741 A1* | 6/2010 | Slowey ............... A61B 10/0045 600/573 |
| 2010/0266449 A1* | 10/2010 | Wu et al. ........................ 422/58 |

FOREIGN PATENT DOCUMENTS

| | | |
|---|---|---|
| JP | 53074794 A | 7/1978 |
| JP | H05094764 U | 12/1993 |
| WO | 2007/072478 A2 | 6/2007 |
| WO | 2010/145191 A1 | 12/2010 |

* cited by examiner

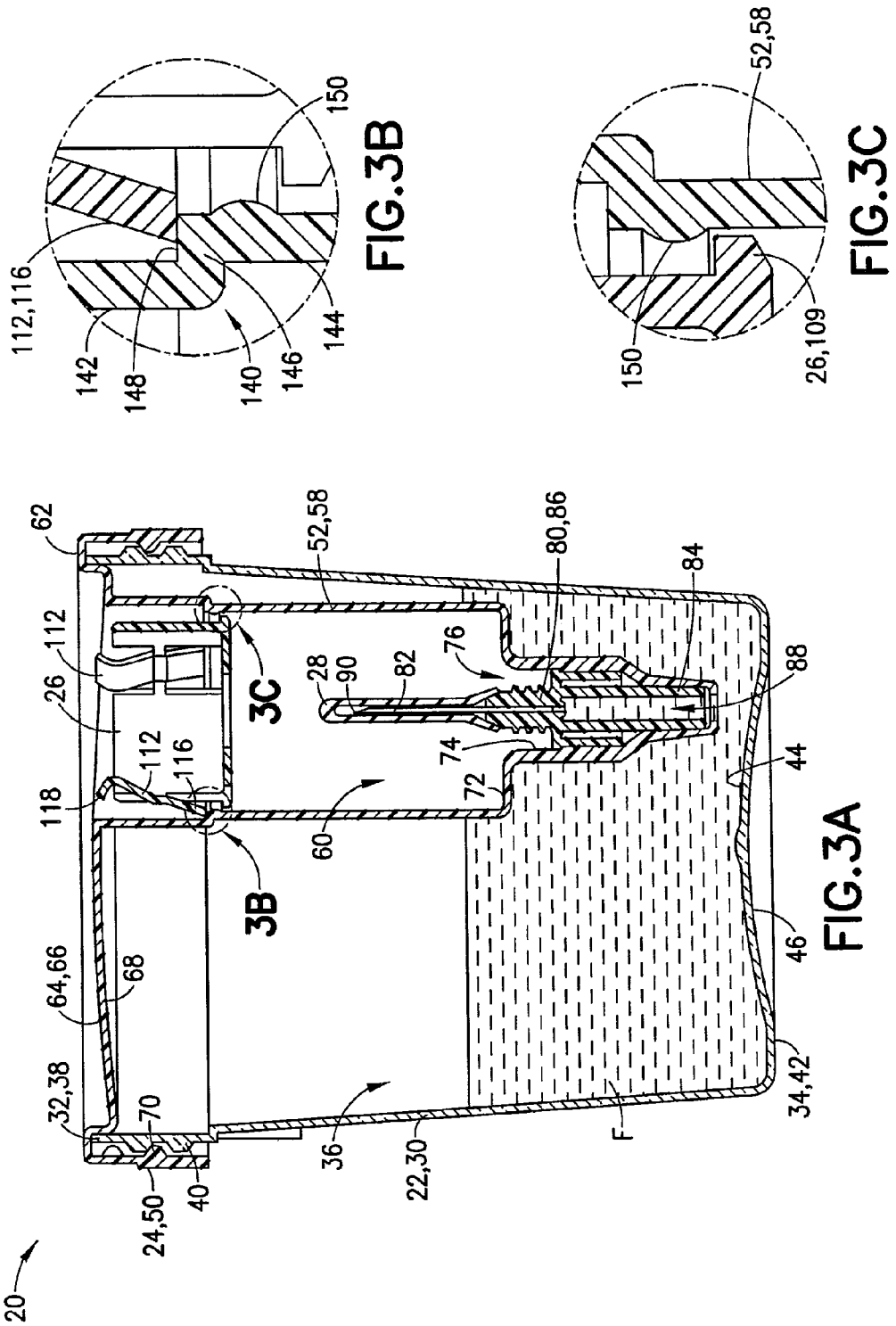

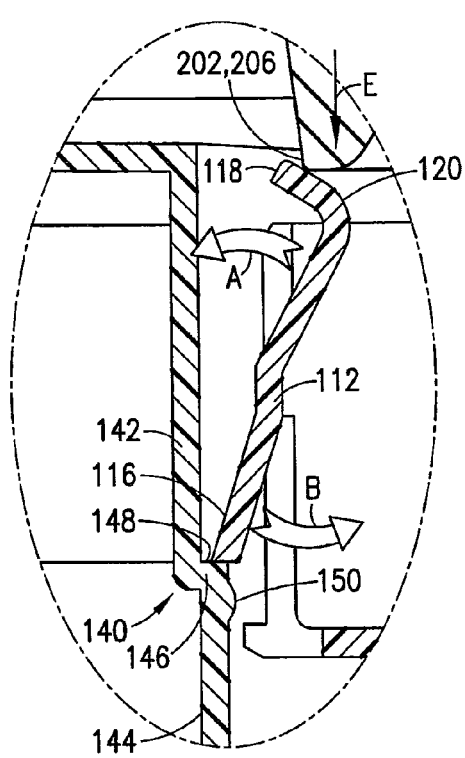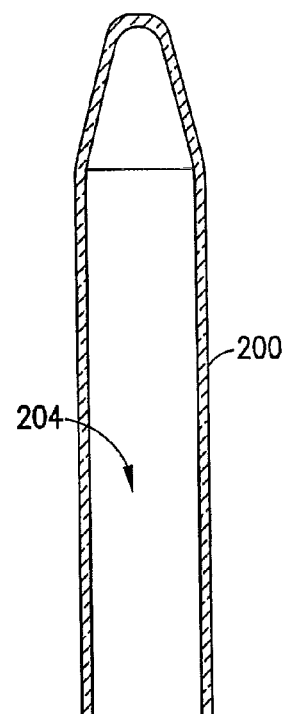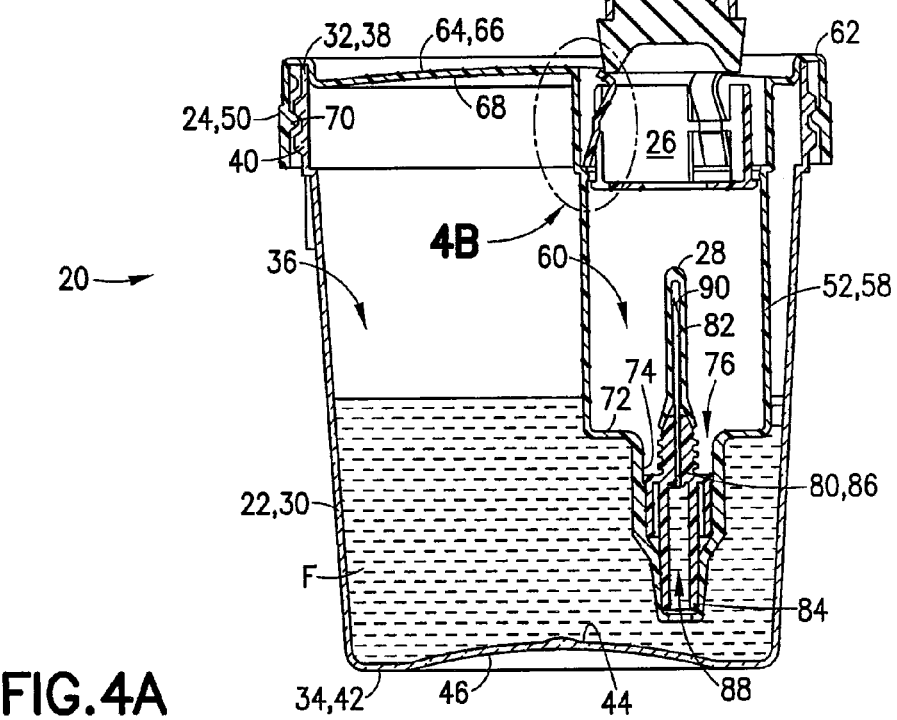
FIG. 4B
FIG. 4A

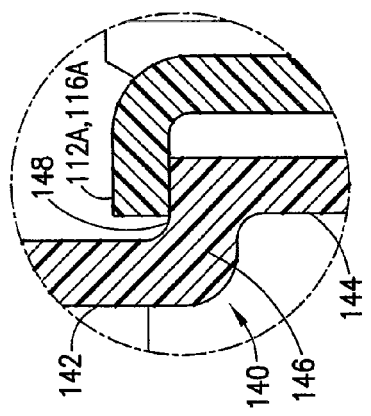
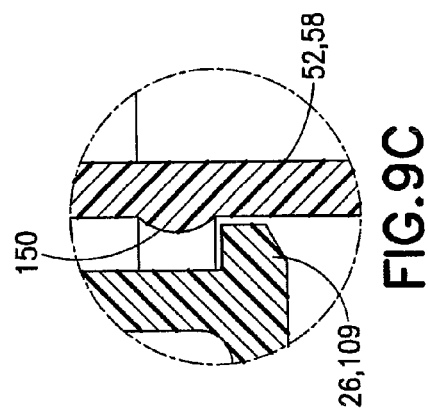
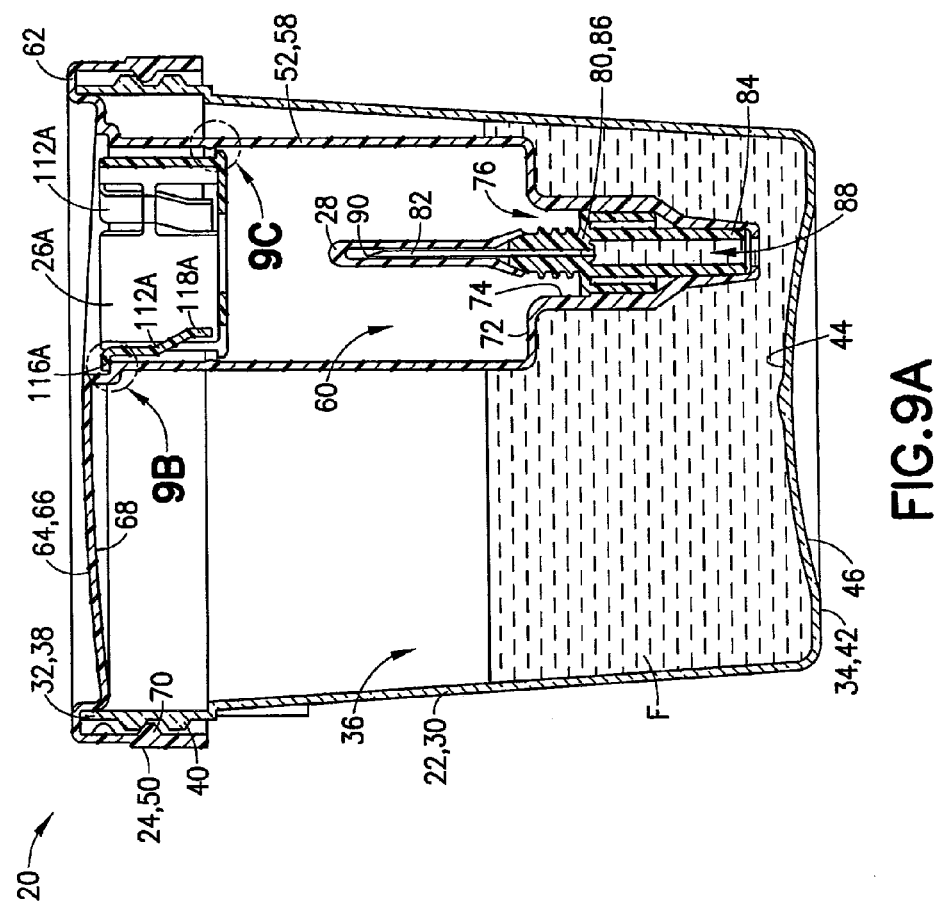

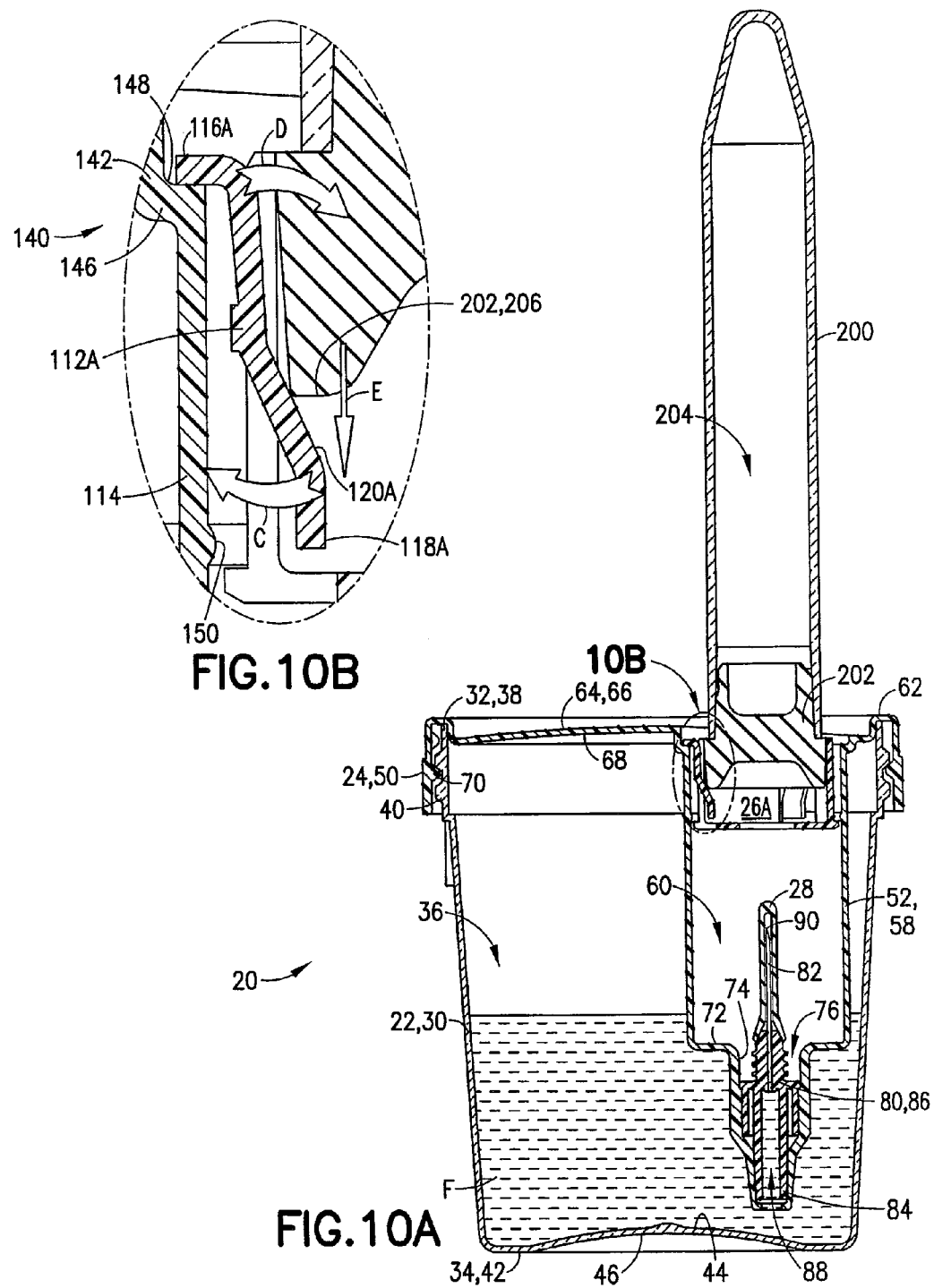

SAFETY SHIELD FOR FLUID SPECIMEN CONTAINER

BACKGROUND OF THE INVENTION

1. Field of the Disclosure

The present disclosure relates generally to a container assembly for collecting a fluid specimen. More particularly, the present disclosure relates to a container assembly including a shield that may be used to cover a needle disposed in the container assembly to prevent re-exposure of the needle.

2. Description of the Related Art

To conduct laboratory testing on biological fluid samples, such as urine, it is necessary to provide a container for collecting the fluid sample. These collection containers typically include a cup-shaped container with a removable cover. Once a fluid sample has been collected in the container, the cover is reapplied. The collection container may then be transported to a laboratory or other testing facility where a sample of the collected specimen is extracted for test purposes.

To simplify the sample extraction process, prior collection containers have used covers which not only cover and seal the collection container, but also provide for the use of an extraction device which permits the extraction of a sample of the fluid specimen. Such covers may include a cavity which supports a tube extending within the cavity to the lower end of the cup-shaped container in fluid communication with the specimen contained within the container. The tube or the cover may include a needle so that an air-evacuated collection device, such as a specimen collection tube, may be attached thereto to draw a portion of the collected sample thereinto without removal of the cover. In these configurations, the sample can be removed without spilling or contaminating the sample and/or cavity area. Subsequent samples may be drawn from the collection container by using a plurality of collection tubes. However, prior collection containers typically include an exposed needle which may result in a patient and/or healthcare worker receiving an inadvertent needle stick injury. Accordingly, there is a need for a collection container assembly which allows for improved collection, transportation, and subsequent dispensing of a fluid specimen.

SUMMARY OF THE INVENTION

The present disclosure provides a container assembly which includes a shield disposed at least partially within a receiving cavity of a receptacle of a lid. The shield provides a physical barrier that at least partially covers and/or blocks an entrance to the receiving cavity to prevent a patient and/or healthcare worker from needle stick injuries. In one embodiment, the shield is adapted to receive a stopper of a collection tube, and the shield is transitionable between a locked position in which the shield is restrained within an open end of the receptacle, and an unlocked position in which the shield is movable within the receiving cavity of the receptacle. In this embodiment, with the shield in the unlocked position, the collection tube is moveable axially within the receiving cavity of the receptacle so that a stopper of the collection tube is pierceable by a cannula disposed within the receiving cavity of the receptacle. In this manner, with the stopper of the collection tube engaged with the cannula, a fluid specimen disposed in a chamber of the container can be transferred to a tube chamber of the collection tube via the cannula.

In accordance with an embodiment of the present invention, a container assembly for collecting a fluid specimen includes a container having a first end, a second end, and a sidewall extending therebetween and defining a chamber for receiving the fluid specimen. The container assembly of this embodiment includes a lid attachable to the container to at least partially close the first end thereof, the lid having an upper surface and an elongate receptacle extending from the upper surface into the chamber of the container, the receptacle having an open end defined within the upper surface of the lid, a lower end, a locking portion, and a wall member defining a receiving cavity and extending between the open end and the lower end, the lower end of the receptacle including a cannula in fluid communication with the chamber of the container. The container assembly further includes a shield disposed at least partially within the receiving cavity of the receptacle, the shield transitionable between a locked position in which the shield is restrained within the open end of the receptacle, and an unlocked position in which the shield is movable within the receiving cavity of the receptacle.

In one configuration, the cannula includes a first end positioned within the receiving cavity and a second end in fluid communication with the chamber of the container. The container assembly further includes a closure member engaged with the first end of the cannula and transitionable between a sealed position in which the closure member prevents fluid communication between the chamber of the container and the receiving cavity of the receptacle, and an open position in which the closure member allows fluid communication between the chamber of the container and the receiving cavity of the receptacle. In one configuration, the shield includes a locking member transitionable from the locked position in which the locking member is engaged with the locking portion of the receptacle so that the shield is restrained within the open end of the receptacle, and the unlocked position in which the locking member is disengaged from the locking portion of the receptacle so that the shield is movable within the receiving cavity of the receptacle. The locking member of the shield may also include a first end and a second end with the first end of the locking member engaging the locking portion of the receptacle in the locked position. In one configuration, actuation of the second end of the locking member in a first direction, pivots the first end of the locking member in a second direction, the second direction being different than the first direction. The locking member may include at least one pivotable latch. In another embodiment, the locking member may include a plurality of pivotable latches disposed about a perimeter of the shield. In the locked position, the shield is locked within the receiving cavity above the first end of the cannula. The shield may include a first shield end having a shield bottom wall defining an aperture. In the unlocked position, the shield is movable within the receiving cavity of the receptacle so that a portion of the cannula extends through the aperture of the shield bottom wall.

In one configuration, the lid includes a sealing portion about a perimeter of the lid to seal the chamber of the container. The lid may be threadingly attachable to the container. In another embodiment, the lid may be interference fit to a portion of the container. The second end of the container further includes a bottom wall having an inner convex shaped surface and an outer concave shaped surface.

In accordance with another embodiment of the present invention, a container assembly for collecting a fluid specimen includes a container having a first end, a second end, and a sidewall extending therebetween and defining a chamber for receiving the fluid specimen. The container assembly of this embodiment includes a lid attachable to the container to at least partially close the first end thereof, the lid having an upper surface and an elongate receptacle extending from the upper surface into the chamber of the container, the receptacle having an open end defined within the upper surface of the lid, a lower end, a locking portion, and a wall member defining a receiving cavity and extending between the open end and the lower end, the lower end of the receptacle including a cannula in fluid communication with the chamber of the container. The container assembly further includes a shield disposed at least partially within the receiving cavity of the receptacle and adapted to receive a stopper of a collection tube, the shield transitionable between a locked position in which the shield is restrained within the open end of the receptacle, and an unlocked position in which the shield is movable within the receiving cavity of the receptacle.

In one configuration, the cannula includes a first end positioned within the receiving cavity and a second end in fluid communication with the chamber of the container. The container assembly further includes a closure member engaged with the first end of the cannula and transitionable between a sealed position in which the closure member prevents fluid communication between the chamber of the container and the receiving cavity of the receptacle, and an open position in which the closure member allows fluid communication between the chamber of the container and the receiving cavity of the receptacle. In one configuration, the shield includes a locking member transitionable from the locked position in which the locking member is engaged with the locking portion of the receptacle so that the shield is restrained within the open end of the receptacle, and the unlocked position in which the locking member is disengaged from the locking portion of the receptacle so that the shield is movable within the receiving cavity of the receptacle. In one embodiment, with the shield restrained within the open end of the receptacle in the locked position and the stopper of the collection tube received within the shield and moved axially within the receiving cavity of the receptacle, the stopper disengages the locking member of the shield from the locking portion of the receptacle to move the locking member from the locked position to the unlocked position. With the locking member of the shield in the unlocked position, the collection tube is moveable axially within the receiving cavity of the receptacle so that the stopper of the collection tube is engaged with the first end of the cannula, wherein the stopper is pierceable by the first end of the cannula.

In accordance with another embodiment of the present invention, a container assembly for collecting a fluid specimen includes a container having a first end, a second end, and a sidewall extending therebetween and defining a chamber for receiving the fluid specimen. The container assembly of this embodiment includes a lid attachable to the container to at least partially close the first end thereof, the lid having an upper surface and an elongate receptacle extending from the upper surface into the chamber of the container, the receptacle having an open end defined within the upper surface of the lid, a lower end, and a wall member defining a receiving cavity and extending between the open end and the lower end, the lower end of the receptacle including a cannula in fluid communication with the chamber of the container. The container assembly further includes a shield disposed at least partially within the receiving cavity of the receptacle, the shield transitionable between a first position in which the shield is spaced a distance from the cannula, and a second position in which the shield is disposed at least partially about the cannula.

BRIEF DESCRIPTION OF THE DRAWINGS

FIG. 3A is a cross-sectional view of the container assembly of FIG. 1 taken along line 3A-3A of FIG. 2 in accordance with an embodiment of the present invention.

FIG. 3B is an enlarged partial cross-sectional view of the container assembly of FIG. 1 taken along section 3B of FIG. 3A in accordance with an embodiment of the present invention.

FIG. 3C is an enlarged partial cross-sectional view of the container assembly of FIG. 1 taken along section 3C of FIG. 3A in accordance with an embodiment of the present invention.

FIG. 4A is the cross-sectional view of FIG. 3A, with a stopper of a collection tube engaging a portion of a shield in a locked position in accordance with an embodiment of the present invention.

FIG. 4B is an enlarged partial cross-sectional view of the container assembly of FIG. 4A taken along section 4B in accordance with an embodiment of the present invention.

FIG. 9A is a cross-sectional view of the container assembly of FIG. 7 taken along line 9A-9A of FIG. 8 in accordance with an embodiment of the present invention.

FIG. 9B is an enlarged partial cross-sectional view of the container assembly of FIG. 7 taken along section 9B of FIG. 9A in accordance with an embodiment of the present invention.

FIG. 9C is an enlarged partial cross-sectional view of the container assembly of FIG. 7 taken along section 9C of FIG. 9A in accordance with an embodiment of the present invention.

FIG. 10A is the cross-sectional view of FIG. 9A, with a stopper of a collection tube engaging a portion of a shield in a locked position in accordance with an embodiment of the present invention.

FIG. 10B is an enlarged partial cross-sectional view of the container assembly of FIG. 10A taken along section 10B in accordance with an embodiment of the present invention.

DETAILED DESCRIPTION

Figure 1:
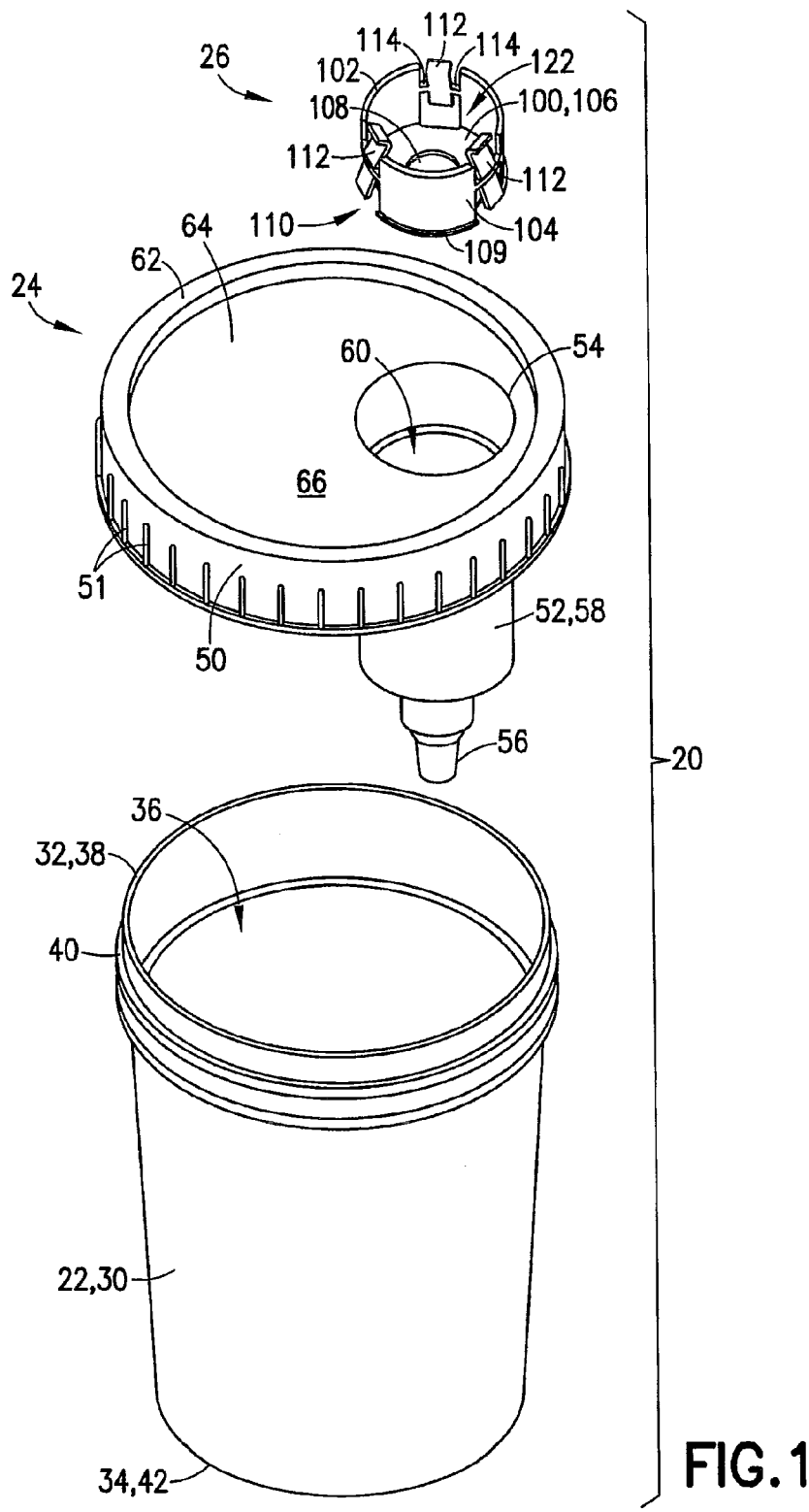
FIG. 1 is an exploded, perspective view of a container assembly in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-3A, a container assembly 20 includes a container 22, a lid 24, a shield 26, and a closure or sleeve member 28. An exemplary container assembly in accordance with the present disclosure may be used to safely collect a fluid specimen, transport the fluid specimen, and draw a sample of the fluid specimen without contamination of the fluid specimen and without receiving a needle stick injury.

Referring to FIGS. 1-3A, container 22 generally includes a sidewall 30 extending between a first, open end 32 and a second, closed end 34. Sidewall 30 defines interior or collection chamber 36 for receiving a fluid specimen such as fluid specimen F (FIGS. 3A-6). In one embodiment, sidewall 30 of container 22 comprises a slightly tapering, tubular vessel having continuous, tapered sidewalls 30. Open end 32 defines a lip 38 and includes an exterior threaded portion 40 around a perimeter thereof. Closed end 34 comprises a bottom wall 42 having a convex shaped inner surface 44 and a concave shaped outer surface 46 to assist in maximum sample collection of small volume fluids in the bottom of container 22. In one embodiment, collection chamber 36 of container 22 is suitable for holding biologically hazardous materials. In one embodiment, container 22 and lid 24 may be formed from any conventional material such as, for example, a polymeric resin. Polymeric resins are well known in the art and include, for example, polyethylene, polycarbonate, polystyrene, and similar polymeric resinous materials.

In one embodiment, sidewall 30 of container 22 may contain a fill level indicator (not shown) which identifies a maximum fill level for collecting a fluid specimen such as fluid specimen F (FIGS. 4A-6). The fill level indicator is positioned so that the fluid specimen will not exceed the capacity of collection chamber 36 when container 22 is filled and lid 24 is attached to container 22.

Referring to FIGS. 1-3A, lid 24 generally includes a flange 50 extending around its outer rim and is sized to provide a tight fit when lid 24 is placed over container 22. Flange 50 of lid 24 includes ribs 51 disposed on an exterior surface of flange 50. Ribs 51 of lid 24 provide a gripping means to allow a user or a tool to more easily grasp lid 24 when attaching lid 24 to container 22. Lid 24 also includes an elongate receptacle 52 extending into container 22 towards bottom wall 42 of container 22. Receptacle 52 includes an open end 54, an opposing lower end 56, and a wall member 58 extending from open end 54 to lower end 56 and defining a receiving cavity 60. In one embodiment, receiving cavity 60 is sized and shaped to receive a portion of shield 26 and a collection tube 200 including a stopper 202 and defining a tube chamber 204 (FIGS. 4A-6 and 10A-12) as will be described in more detail below.

Referring to FIGS. 1-3A, in one embodiment, lid 24 comprises a generally disc-shaped component having an outer or peripheral zone 62 and an inner or central zone 64 including an upper surface 66 and an opposing under surface 68 (FIGS. 3A and 9A). Flange 50 extends downward from peripheral zone 62 of lid 24. Referring to FIG. 3A, in one embodiment, flange 50 extends downward from peripheral zone 62 to partially hide under surface 68 of lid 24. Flange 50 includes an inner surface which contains a means for sealingly engaging lid 24 with open end 32 of container 22. In one embodiment, flange 50 of lid 24 includes an interior threaded portion 70 (FIGS. 3A, 4A, 5, and 6). In such an embodiment, lid 24 is threadingly connectable to open end 32 of container 22 via mating threaded portions 40, 70 as shown in FIG. 3A. In other embodiments, the sealing portion of lid 24 may include a snap fit mechanism, a ball detent, an interference fit mechanism, locking tabs, a spring loaded locking mechanism, a latch, or other similar mechanism to sealingly engage lid 24 to container 22, i.e., to prevent a fluid specimen contained within container 22 and lid 24 from leaking out and to prevent contaminants from getting in.

Figure 2:
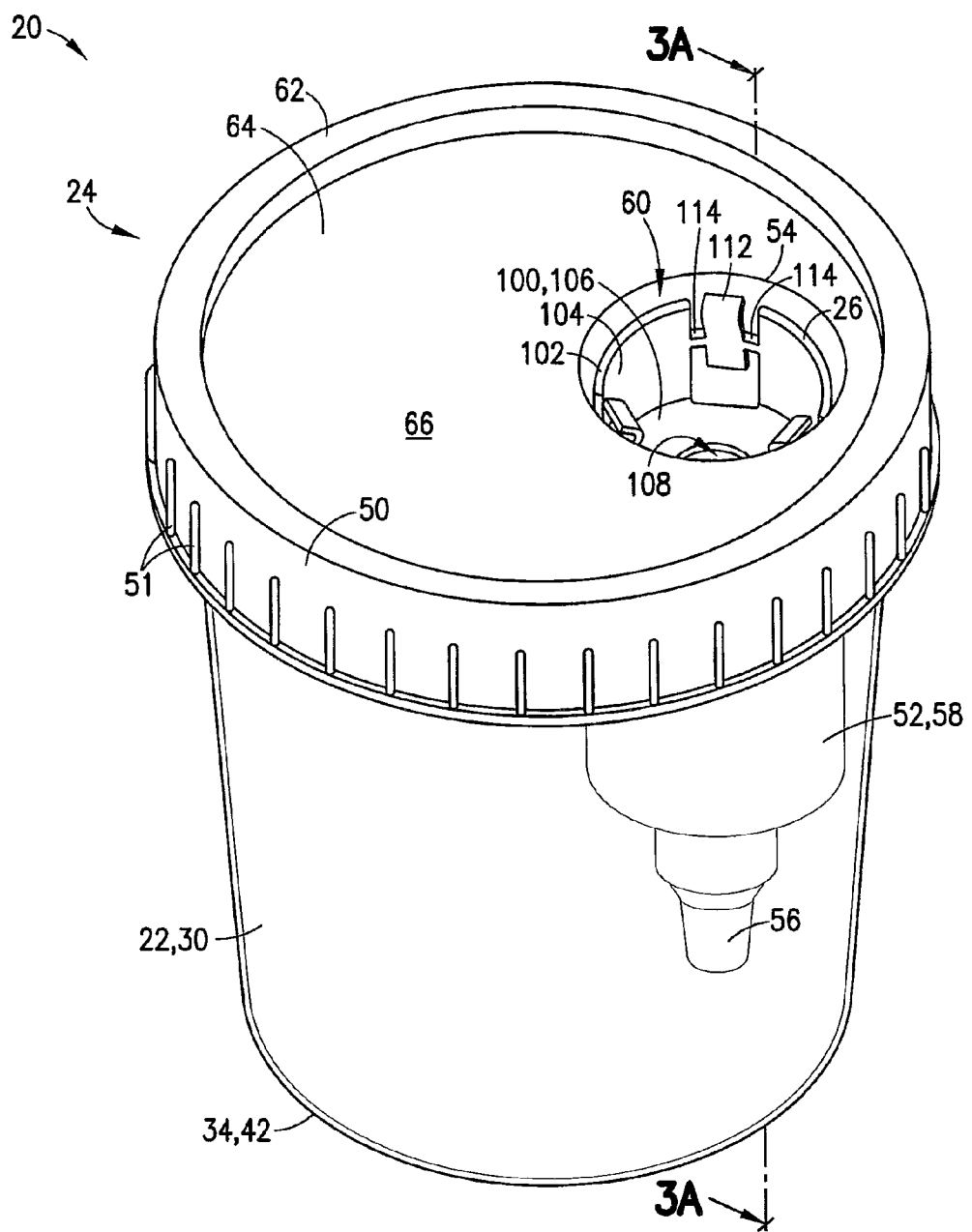
FIG. 2 is an assembled, perspective view of the container assembly of FIG. 1, with a shield in a locked position in accordance with an embodiment of the present invention.

Open end 54 of receptacle 52 is disposed at central zone 64. Referring to FIG. 2, in one embodiment, open end 54 of receptacle 52 is offset towards peripheral zone 62. Wall member 58 of receptacle 52 which defines receiving cavity 60 is continuous with and part of the molded surface of lid 24. Open end 54 of receptacle 52 is defined within upper surface 66 of lid 24 and receptacle 52 extends from upper surface 66 into chamber 36 of container 22, with lid 24 attached to container 22. Referring to FIG. 3B, in one embodiment, receptacle 52 includes a locking portion 140 having a first locking portion vertical wall 142, a second locking portion vertical wall 144, and a locking portion horizontal wall 146 extending between vertical walls 142, 144 and defining a locking surface 148. Referring to FIGS. 3B and 3C, in one embodiment, second vertical wall 144 and wall member 58 of receptacle 52 include a retention ring 150 as will be described in more detail below.

Referring to FIG. 3A, wall member 58 of receptacle 52 includes a cannula end horizontal wall 72 and a cannula end vertical wall 74 which together define a cannula opening 76 in which a cannula 80 is received. In one embodiment, cannula 80 is continuous with and part of receptacle 52. Cannula 80 generally includes a first end 82, an opposing second end 84, and a cannula wall 86 extending from first end 82 to second end 84. Cannula wall 86 defines an elongate aperture 88 which spans the extent of cannula 80 so that cannula 80 is cannulated along its entire length. In this manner, elongate aperture 88 is in fluid communication with chamber 36 of container 22. In one embodiment, first end 82 of cannula 80 projects from cannula end horizontal wall 72 into receptacle 52 in a position to pierce stopper 202 of collection tube 200 when collection tube 200 is received within receiving cavity 60 of receptacle 52. With collection tube 200 received within receiving cavity 60 and with stopper 202 pierced by first end 82 of cannula 80, chamber 36 of container 22 is in fluid communication with tube chamber 204 of collection tube 200 via elongate aperture 88 of cannula 80 as will be described in more detail below. In one embodiment, first end 82 of cannula 80 comprises needle point 90 to pierce stopper 202 of collection tube 200.

Referring to FIGS. 1-3A, shield 26 generally includes a first shield end 100, an opposing second shield end 102, and a shield sidewall 104 extending from end 100 to end 102. First shield end 100 includes a shield bottom wall 106 which defines an aperture 108 and includes a protruding ring portion 109 which extends outward from shield bottom wall 106. Referring to FIG. 1, in one embodiment, shield bottom wall 106 defines aperture 108 in a central region. Aperture 108 is sized to receive first end 82 of cannula 80 therethrough as will be described in more detail below. In one embodiment, referring to FIG. 1, shield sidewall 104 includes a plurality of sections defining receiving slots 110 therebetween. Receiving slots 110 are sized to receive a locking member 112 therein. In one embodiment, locking member 112 can be pivotably secured between adjacent sections of shield sidewall 104 via connection members 114 so that locking member 112 can be pivoted from a first, locked position to a second, unlocked position as will be described in more detail below. Referring to FIG. 4B, each locking member 112 includes a locking end 116 and an opposing engagement end 118 including an interior engagement surface 120.

Shield bottom wall 106 and shield sidewall 104 together define a shield receiving cavity 122 which is sized and adapted to receive a portion of stopper 202 of collection tube 200 as will be described in more detail below. Referring to FIG. 1, in one embodiment, locking member 112 of shield 26 may comprise at least one pivotable latch. In other embodiments, locking member 112 may comprise a plurality of pivotable or flexible latches disposed about a perimeter of shield 26. Locking member 112 may be integral to shield 26 and may be molded from plastic or stamped from metal. Referring to FIG. 1, in one embodiment, locking members 112 are movably mounted relative to shield sidewall 104 via connection members 114 so that each locking member 112 may be simultaneously pivoted or flexed to allow for complete unlatching of shield 26 as will be described in more detail below. In this manner, shield 26 may be transitionable between a locked position in which a portion of shield 26 may be restrained within open end 54 of receptacle 52, and an unlocked position in which shield 26 is movable within receiving cavity 60 of receptacle 52.

Referring to FIG. 3A, sleeve member 28 generally includes a self-sealing sleeve secured over cannula 80 so that sleeve member 28 covers needle point 90 of first end 82 of cannula 80 in a sealed position to prevent fluid communication between chamber 36 of container 22 and receiving cavity 60 of receptacle 52. Sleeve member 28 is pierceable by needle point 90 of cannula 80 so that sleeve member 28 is transitionable from the sealed position to an open position in which sleeve member 28 allows fluid communication between chamber 36 of container 22 and receiving cavity 60 of receptacle 52. Also, with sleeve member 28 in such an open position, tube chamber 204 of collection tube 200 may be in fluid communication with chamber 36 of container 22 when collection tube 200 is inserted in receiving cavity 60 of receptacle 52 and stopper 202 is pierced by needle point 90 of cannula 80 as will be discussed in more detail below.

In one embodiment, sleeve member 28 comprises a resilient material. For example, sleeve member 28 is preferably a unitary device molded of any flexible, elastomeric material conventionally used for fabricating gas-proof closures. Sleeve member 28 may be formed of a natural rubber material, polyurethane elastomers, butyl rubbers, or similar materials. It is contemplated that sleeve member 28 is formed of a material having a Shore A hardness of approximately 35 to 80. It is also envisioned that sleeve member 28 can have other material hardness values that would provide an appropriate self-sealing material to prevent fluid communication between chamber 36 of container 22 and receiving cavity 60 of receptacle 52 with sleeve member 28 in a sealed position, and allow fluid communication therebetween with sleeve member 28 in an open position.

Referring to FIGS. 3A-3C, the use of shield 26 to cover and/or block the entrance to receiving cavity 60 of receptacle 52 containing needle point 90 of cannula 80 will now be described. Shield 26 may be positioned at least partially within receiving cavity 60 of receptacle 52. In a locked position, shield 26 is restrained within receiving cavity 60 of receptacle 52. For example, in the locked position, locking members 112 of shield 26 are orientated as shown in FIGS. 3A and 3B so that locking end 116 of locking member 112 engages locking surface 148 of locking portion 140 of receptacle 52 as shown in FIG. 3B. In this manner, shield 26 is restrained within receiving cavity 60 of receptacle 52, i.e., significant relative movement between shield 26 and receptacle 52 is prevented. In one embodiment, referring to FIG. 3C, wall member 58 includes retention ring 150 which provides a physical barrier to resist movement of protruding ring portion 109 of shield 26. In this manner, retention ring 150 provides an additional securement mechanism to restrain shield 26 within receiving cavity 60 of receptacle 52 in the locked position.

In the locked position, shield 26 is particularly advantageous in that it allows a user, such as a patient and/or healthcare worker, to safely handle container assembly 20 without receiving needle stick injuries from needle point 90 of cannula 80. With shield 26 in the locked position as described above, shield 26 provides a physical barrier preventing the fingers of a user from being inserted within receiving cavity 60 of receptacle 52 and contacting needle point 90 of cannula 80. In this manner, the user is prevented from needle stick injuries and the user can conveniently and safely handle container assembly 20 and withdraw a fluid sample from chamber 36 of container 22 into a collection tube 200 as will be described in more detail below.

Referring to FIGS. 4A-6, the use of container assembly 20 and collection tube 200 to withdraw a fluid specimen F from chamber 36 of container 22 into tube chamber 204 of collection tube 200 will now be described.

Container assembly 20 is intended to be used in the first instance by a patient, and then by a doctor, nurse, or laboratory technician in the second instance for sampling of the collected fluid specimen in container 22. The patient uses container 22 by removing lid 24 and then providing the fluid specimen. Lid 24 can then be attached to container 22, and container assembly 20 containing fluid specimen F given to the test person. At this time, when the test person is ready to draw the fluid specimen for testing, collection tube 200 including stopper 202 having an exterior engagement surface 206 (FIG. 4B) and defining tube chamber 204 is inserted into open end 54 of receptacle 52 as shown in FIG. 4A.

Figure 5:
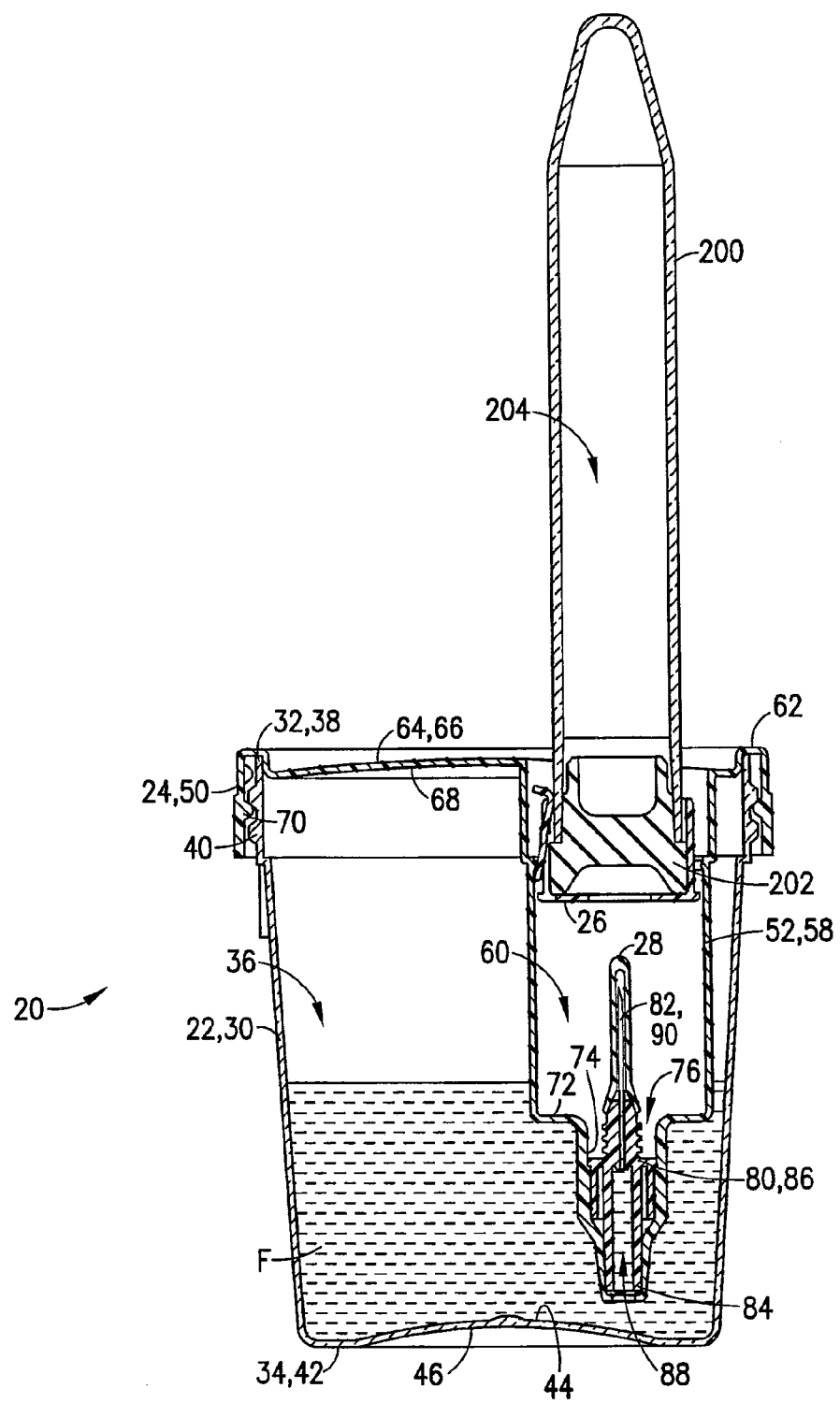
FIG. 5 is the cross-sectional view of FIG. 4A, with the shield in an unlocked position in accordance with an embodiment of the present invention.
Figure 6:
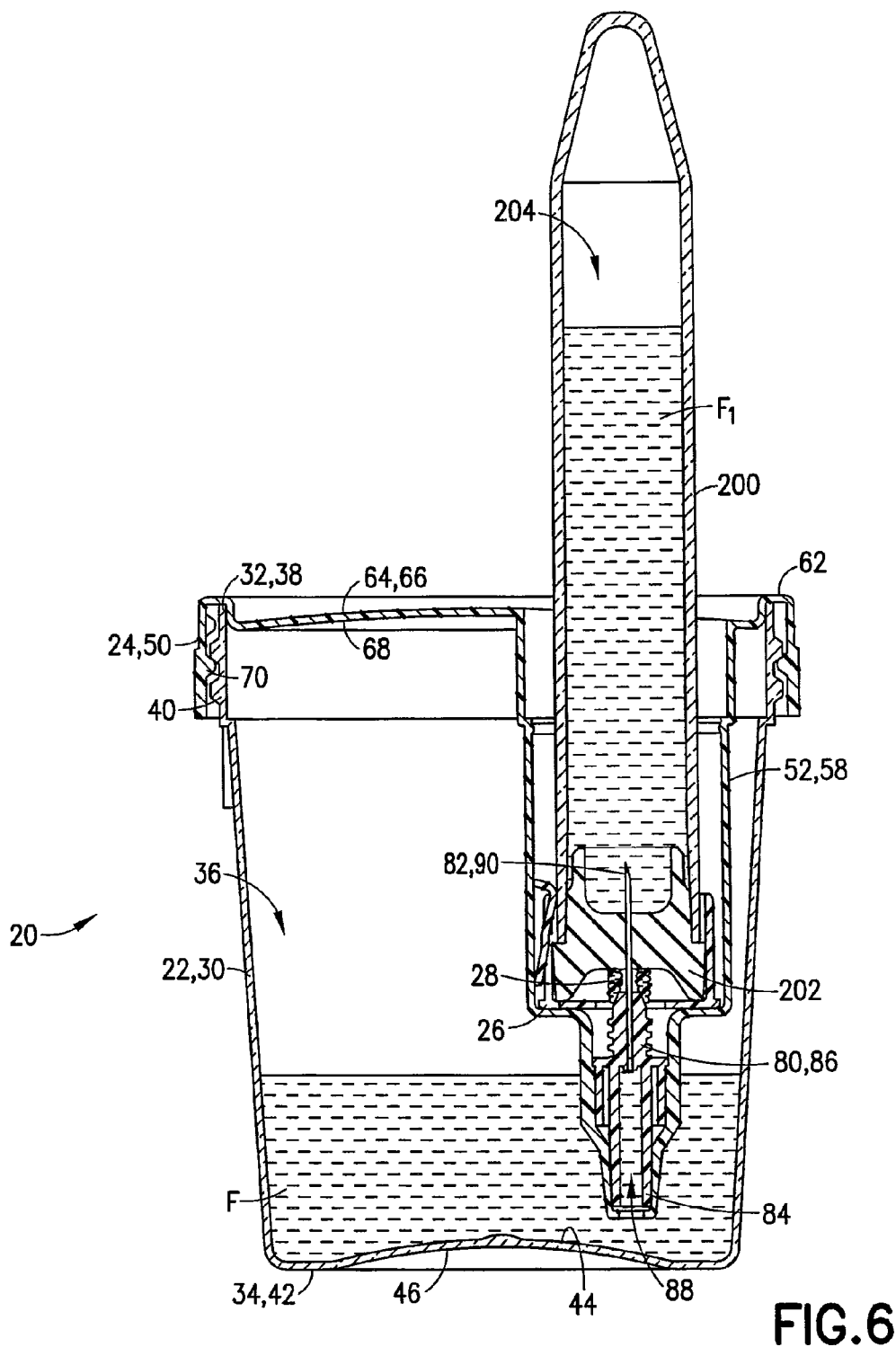
FIG. 6 is the cross-sectional view of FIG. 4A, with the stopper of the collection tube engaging a cannula in accordance with an embodiment of the present invention.
Figure 7:
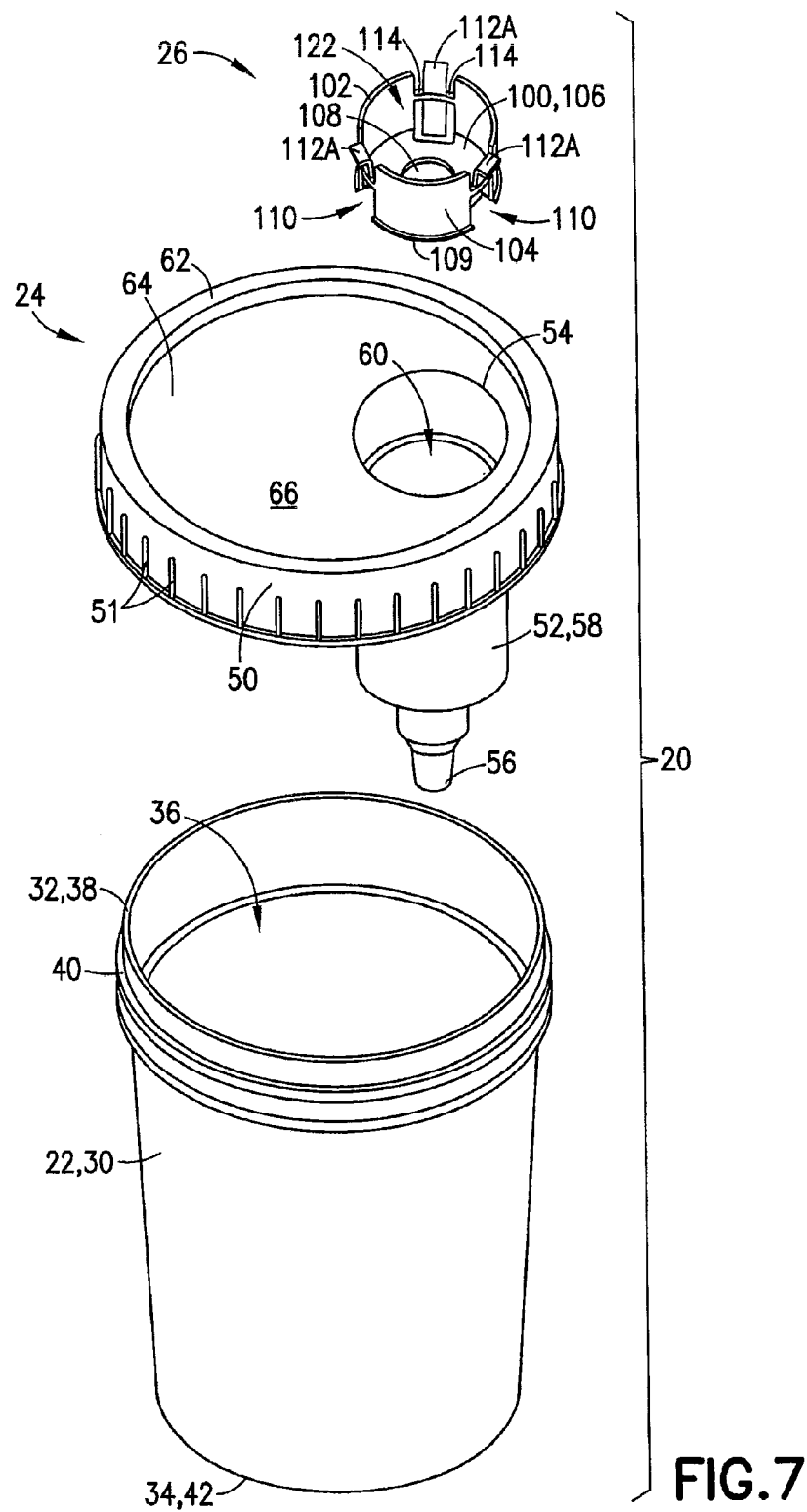
FIG. 7 is an exploded perspective view of a container assembly in accordance with an embodiment of the present invention.
Figure 8:
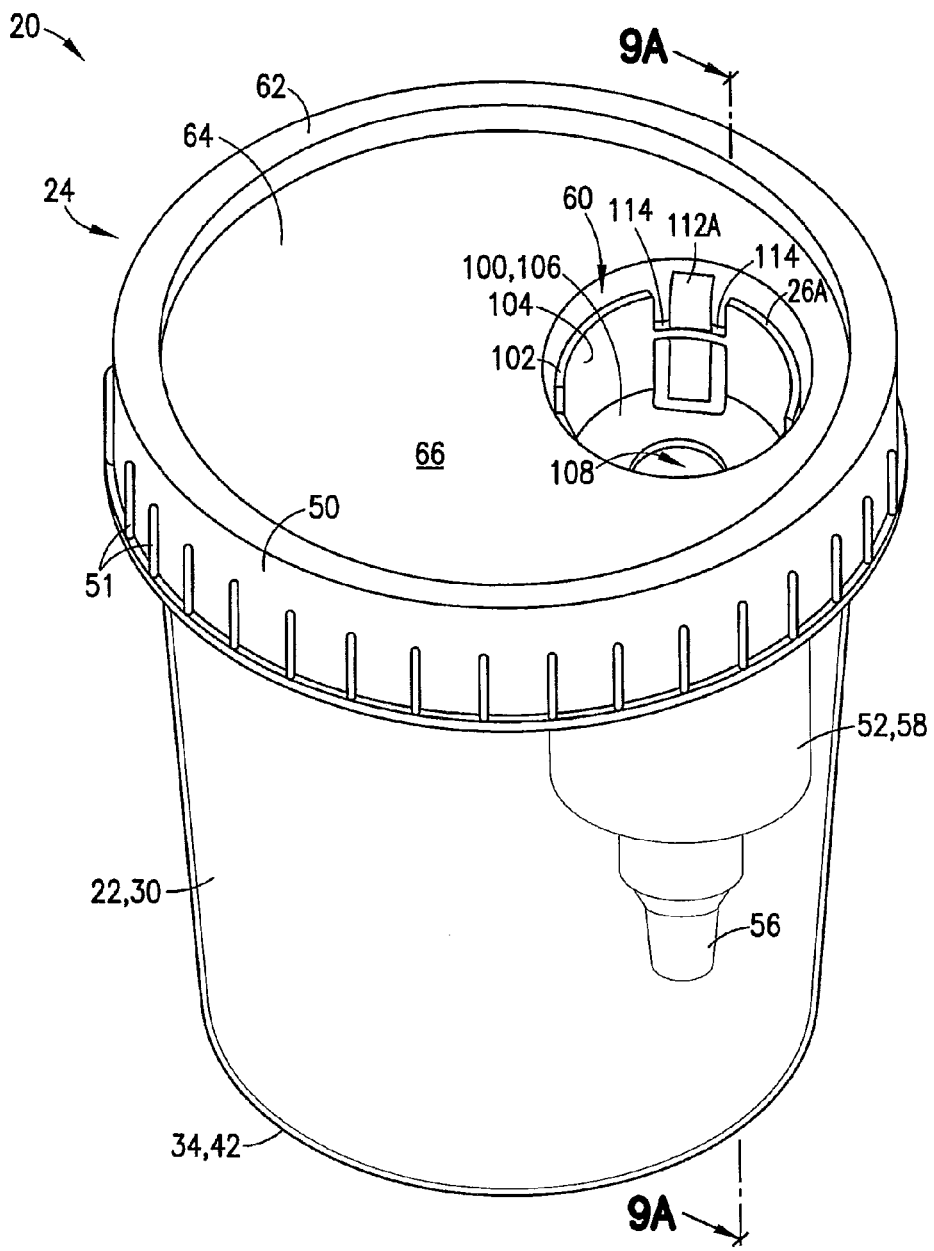
FIG. 8 is an assembled perspective view of the container assembly of FIG. 7 in accordance with an embodiment of the present invention.

Once shield 26 is disposed at least partially within receiving cavity 60 of receptacle 52 in the locked position as described above and stopper 202 of collection tube 200 is positioned adjacent to receiving cavity 122 (FIG. 1) of shield 26 as shown in FIGS. 4A and 4B, collection tube 200 can be moved axially into receiving cavity 60 of receptacle 52. Referring to FIGS. 4A and 4B, as collection tube 200 is moved into receiving cavity 60 of receptacle 52 in a direction generally along arrow E (FIG. 4B), exterior engagement surface 206 of stopper 202 cooperates with interior engagement surface 120 of each locking member 112 of shield 26 and actuates or pushes engagement end 118 of locking member 112 outward in a direction generally along arrow A. Movement of engagement end 118 of locking member 112 of shield 26 in the direction generally along arrow A causes locking end 116 of locking member 112 of shield 26 to pivot or move in a direction generally along arrow B (FIG. 4B) so that locking end 116 disengages from locking surface 148 of locking portion 140 of receptacle 52. In this manner, shield 26 is transitioned from the locked position shown in FIGS. 3A and 3B to the unlocked position as shown in FIGS. 5 and 6. In this manner, stopper 202 of collection tube 200 functions as a key to unlock shield 26 from the locked position to allow shield 26 and collection tube 200 to move within receiving cavity 60 of receptacle 52 as shown in FIGS. 5 and 6. Stopper 202 of collection tube 200 cooperates with shield 26 to enable each locking member 112 of shield 26 to be simultaneously moved from the locked position shown in FIGS. 3A and 3B to the unlocked position shown in FIGS. 5 and 6. In one embodiment, shield 26 is sized and shaped to be engageable with stopper 202 of collection tube 200 in the manner described above, but not to allow interaction with a human finger to unlock shield 26 from its locked position relative to receptacle 52. Further, shield 26 is sized and shaped so that a human finger would not be able to function as a key to simultaneously unlock each of locking members 112 of shield 26.

With the locking members 112 of shield 26 in the unlocked position, collection tube 200 can be further moved axially within receiving cavity 60 of receptacle 52 as shown in FIGS. 5 and 6 until stopper 202 engages first end 82 of cannula 80 as shown in FIG. 6. Because needle point 90 of cannula 80 projects into receiving cavity 60 of receptacle 52 as discussed above, as collection tube 200 is moved within receiving cavity 60 of receptacle 52, needle point 90 is capable of piercing stopper 202 of collection tube 200 so that chamber 36 of container 22 is in fluid communication with tube chamber 204 of collection tube 200 via elongate aperture 88 of cannula 80. This fluid communication is established because as collection tube 200 is inserted within receiving cavity 60 of receptacle 52 so that stopper 202 engages first end 82 of cannula 80, stopper 202 of collection tube 200 engages and pushes down sleeve member 28 over first end 82 of cannula 80 as shown in FIG. 6. Because sleeve member 28 is formed from a resilient flexible material, when collection tube 200 is removed from receiving cavity 60 of receptacle 52, sleeve member 28 is capable of returning to its original position to re-seal and prevent fluid communication between elongate aperture 88 of cannula 80 and receiving cavity 60 of receptacle 52 as shown in FIGS. 4A and 5.

With collection tube 200 positioned as shown in FIG. 6 with needle point 90 of cannula 80 piercing stopper 202, a test person may draw or transfer fluid specimen F from chamber 36 of container 22 into tube chamber 204 of collection tube 200 (FIG. 6, fluid specimen $F_1$). Once the desired amount of the fluid specimen $F_1$ is received within tube chamber 204 as shown in FIG. 6, collection tube 200 can then be withdrawn or retracted from receiving cavity 60 of receptacle 52. If needed, a second, third, etc., collection tube can be inserted and forced over needle point 90 as described above to withdraw additional portions of the fluid specimen F contained within chamber 36 of container 22. Once the final desired portion of fluid specimen F is withdrawn, container assembly 20 may then be discarded or further handled as desired with shield 26 in the locked position, as shown in FIGS. 3A and 3B, to prevent needle stick injuries to the user. In one embodiment, shield 26 is returned to its locked position relative to receptacle 52 via engagement with stopper 202 of collection tube 200 as shown in FIGS. 4A-6. In such an embodiment, retention ring 150 provides a physical barrier that prevents shield 26 from being removed from receptacle 52. In other embodiments, a spring, such as a coil compression spring, may be used to safely return shield 26 to its locked position.

FIGS. 7-12 illustrate another exemplary embodiment of shield 26. The embodiment illustrated in FIGS. 7-12 includes similar components to the embodiment illustrated in FIGS. 1-6, and the similar components are denoted by the same reference numbers used in FIGS. 1-6. Components of the alternate embodiment of shield 26 are denoted by a reference number followed by the letter "A".

Figure 11:
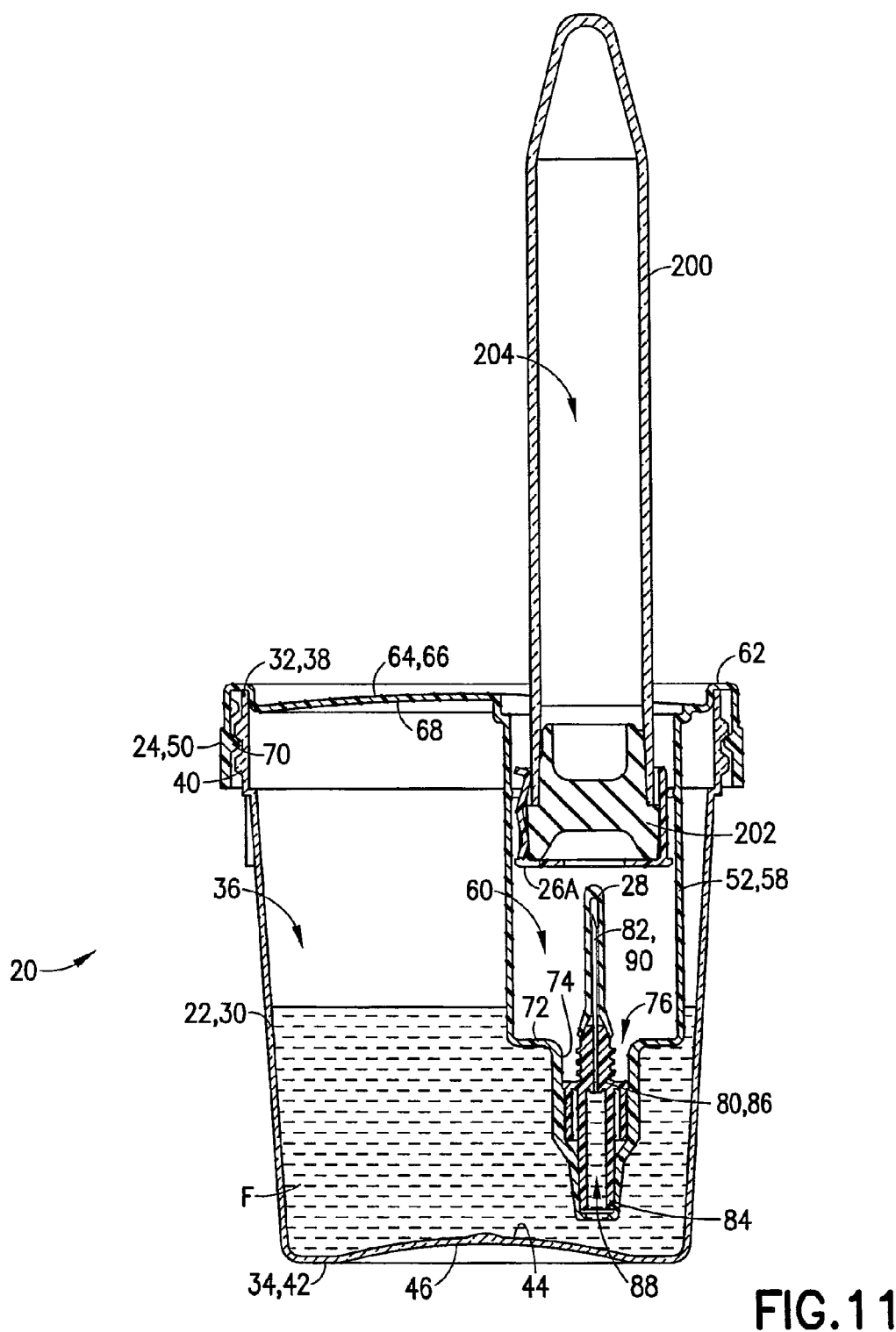
FIG. 11 is the cross-sectional view of FIG. 10A, with the shield in an unlocked position in accordance with an embodiment of the present invention.
Figure 12:
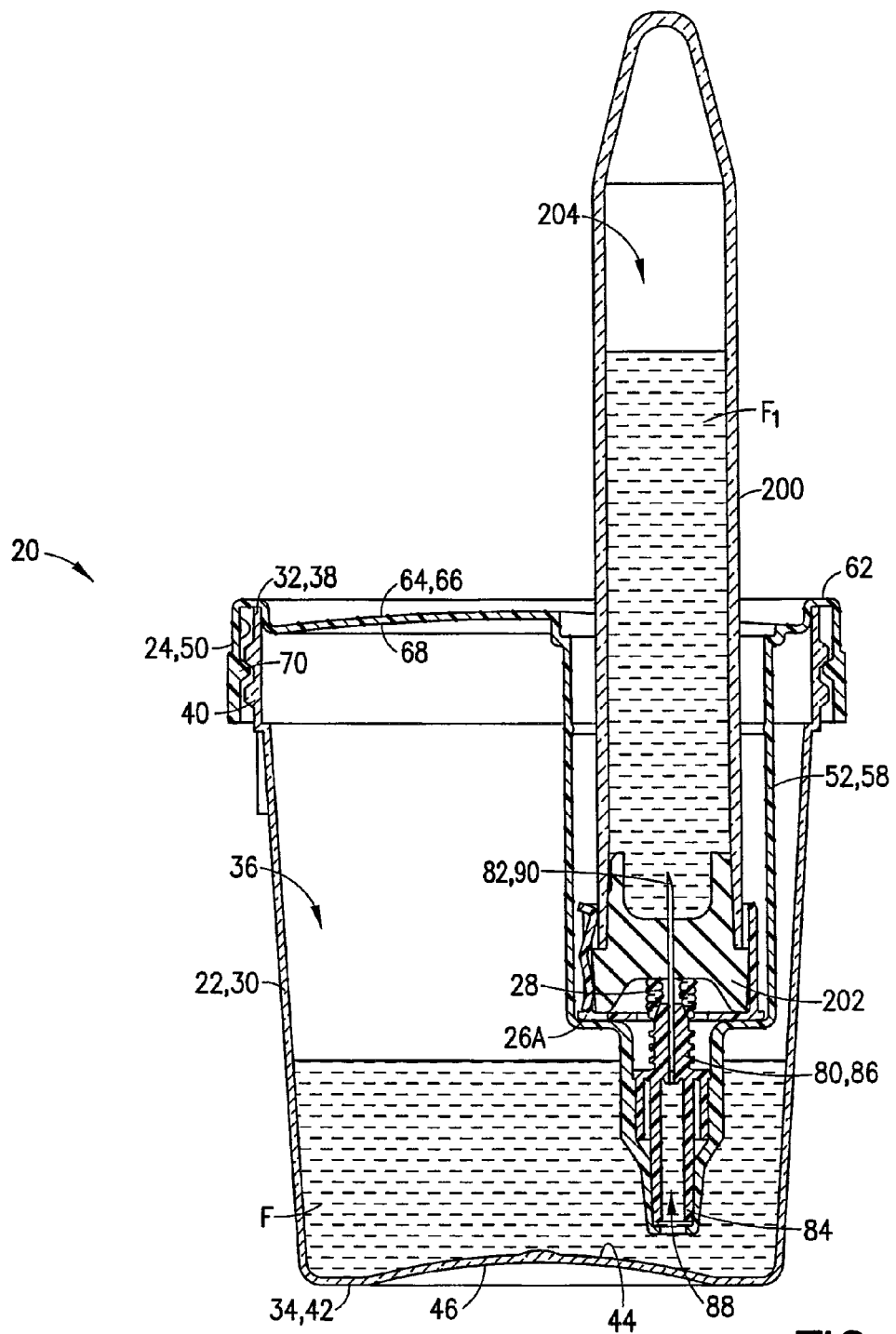
FIG. 12 is the cross-sectional view of FIG. 10A, with the stopper of the collection tube engaging a cannula in accordance with an embodiment of the present invention.

Referring to FIGS. 7-10B, a shield 26A includes a locking end 116A and opposing an engagement end 118A. As shown in FIG. 9B, an upper region of a locking member 112A includes locking end 116A which engages locking surface 148 of locking portion 140 of receptacle 52. In a manner similar as described above regarding shield 26, with stopper 202 of collection tube 200 inserted in the position shown in FIGS. 10A and 10B, as collection tube 200 is moved into receiving cavity 60 of receptacle 52 in a direction generally along arrow E (FIG. 10B), exterior engagement surface 206 of stopper 202 cooperates with an interior engagement surface 120A of each locking member 112A of shield 26A and actuates or pushes engagement end 118A of locking member 112A outward in a direction generally along arrow C. Movement of engagement end 118A of locking member 112A of shield 26A in the direction generally along arrow C causes locking end 116A of locking member 112A of shield 26A to pivot or move in a direction generally along arrow D (FIG. 10B) so that locking end 116A disengages from locking surface 148 of locking portion 140 of receptacle 52. In this manner, shield 26A is transitioned from the locked position shown in FIGS. 9A and 9B to the unlocked position as shown in FIGS. 11 and 12. In this manner, stopper 202 of collection tube 200 functions as a key to unlock shield 26A from the locked position to allow shield 26A and collection tube 200 to move within receiving cavity 60 of receptacle 52 as shown in FIGS. 11 and 12.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A container assembly for collecting a fluid specimen, comprising:
   a container having a first end, a second end, and a sidewall extending therebetween and defining a chamber for receiving the fluid specimen;
   a lid attachable to the container to at least partially close the first end thereof, the lid having an upper surface and an elongate receptacle extending from the upper surface into the chamber of the container, the receptacle having an open end defined within the upper surface of the lid, a lower end, a locking portion, and a wall member defining a receiving cavity and extending between the open end and the lower end, the lower end of the receptacle comprising a cannula in fluid communication with the chamber of the container; and
   a shield having a locking member disposed at least partially within the receiving cavity of the receptacle, wherein with the lid attached to the container, the shield is transitionable between a locked position in which the shield is restrained within the open end of the receptacle, and an unlocked position in which the shield is movable within the receiving cavity of the receptacle, the shield engageable with a separate collection tube which initiates the transition of the shield from the locked position to the unlocked position, wherein the locking member pivots to transition the shield from the locked position to the unlocked position.

2. The container assembly of claim 1, wherein the cannula comprises a first end positioned within the receiving cavity and a second end in fluid communication with the chamber of the container.

3. The container assembly of claim 2, further comprising a closure member engaged with the first end of the cannula and transitionable between a sealed position in which the closure member prevents fluid communication between the chamber of the container and the receiving cavity of the receptacle, and an open position in which the closure member allows fluid communication between the chamber of the container and the receiving cavity of the receptacle.

4. The container assembly of claim 1, wherein the shield comprises a locking member transitionable from the locked position in which the locking member is engaged with the locking portion of the receptacle so that the shield is restrained within the open end of the receptacle, and the unlocked position in which the locking member is disengaged from the locking portion of the receptacle so that the shield is movable within the receiving cavity of the receptacle.

5. The container assembly of claim 4, wherein the locking member of the shield comprises a first end and a second end with the first end of the locking member engaging the locking portion of the receptacle in the locked position.

6. The container assembly of claim 5, wherein actuation of the second end of the locking member in a first direction, pivots the first end of the locking member in a second direction, the second direction being different than the first direction.

7. The container assembly of claim 4, wherein the locking member comprises at least one pivotable latch.

8. The container assembly of claim 4, wherein the locking member comprises a plurality of pivotable latches disposed about a perimeter of the shield.

9. The container assembly of claim 2, wherein, in the locked position, the shield is locked within the receiving cavity above the first end of the cannula.

10. The container assembly of claim 4, wherein the shield includes a first shield end having a shield bottom wall defining an aperture.

11. The container assembly of claim 10, wherein, in the unlocked position, the shield is movable within the receiving cavity of the receptacle so that a portion of the cannula extends through the aperture of the shield bottom wall.

12. The container assembly of claim 1, wherein the lid further comprises a sealing portion about a perimeter of the lid to seal the chamber of the container.

13. The container assembly of claim 12, wherein the lid is threadingly attachable to the container.

14. The container assembly of claim 12, wherein the lid is interference fit to a portion of the container.

15. The container assembly of claim 1, wherein the second end of the container comprises a bottom wall having an inner convex shaped surface and an outer concave shaped surface.

16. A container assembly for collecting a fluid specimen, comprising:
a container having a first end, a second end, and a sidewall extending therebetween and defining a chamber for receiving the fluid specimen;

a lid attachable to the container to at least partially close the first end thereof, the lid having an upper surface and an elongate receptacle extending from the upper surface into the chamber of the container, the receptacle having an open end defined within the upper surface of the lid, a lower end, a locking portion, and a wall member defining a receiving cavity and extending between the open end and the lower end, the lower end of the receptacle comprising a cannula in fluid communication with the chamber of the container; and a shield having a locking member disposed at least partially within the receiving cavity of the receptacle and adapted to receive a stopper of a separate collection tube, wherein with the lid attached to the container, the shield is transitionable between a locked position in which the shield is restrained within the open end of the receptacle, and an unlocked position in which the shield is movable within the receiving cavity of the receptacle, the shield engageable with the collection tube which initiates the transition of the shield from the locked position to the unlocked position, wherein the locking member pivots to transition the shield from the locked position to the unlocked position.

17. The container assembly of claim 16, wherein the cannula comprises a first end positioned within the receiving cavity and a second end in fluid communication with the chamber of the container.

18. The container assembly of claim 17, further comprising a closure member engaged with the first end of the cannula and transitionable between a sealed position in which the closure member prevents fluid communication between the chamber of the container and the receiving cavity of the receptacle, and an open position in which the closure member allows fluid communication between the chamber of the container and the receiving cavity of the receptacle.

19. The container assembly of claim 17, wherein the shield comprises a locking member transitionable from the locked position in which the locking member is engaged with the locking portion of the receptacle so that the shield is restrained within the open end of the receptacle, and the unlocked position in which the locking member is disengaged from the locking portion of the receptacle so that the shield is movable within the receiving cavity of the receptacle.

20. The container assembly of claim 19, wherein, with the shield restrained within the open end of the receptacle in the locked position and the stopper of the collection tube received within the shield and moved axially within the receiving cavity of the receptacle, the stopper disengages the locking member of the shield from the locking portion of the receptacle to move the locking member from the locked position to the unlocked position.

21. The container assembly of claim 20, wherein, with the locking member of the shield in the unlocked position, the collection tube is moveable axially within the receiving cavity of the receptacle so that the stopper of the collection tube is engaged with the first end of the cannula, wherein the stopper is pierceable by the first end of the cannula.

22. A container assembly for collecting a fluid specimen, comprising:
a container having a first end, a second end, and a sidewall extending therebetween and defining a chamber for receiving the fluid specimen;
a lid attachable to the container to at least partially close the first end thereof, the lid having an upper surface and an elongate receptacle extending from the upper surface into the chamber of the container, the receptacle having an open end defined within the upper surface of the lid, a lower end, and a wall member defining a receiving cavity and extending between the open end and the lower end, the lower end of the receptacle comprising a cannula in fluid communication with the chamber of the container; and a shield having a locking member disposed at least partially within the receiving cavity of the receptacle, wherein with the lid attached to the container, the shield is transitionable between a first position in which the shield is spaced a distance from the cannula, and a second position in which the shield is disposed at least partially about the cannula, the shield engageable with a separate collection tube which initiates the transition of the shield from the first position to the second position, wherein the locking member pivots to transition the shield from the locked position to the unlocked position.

23. The container assembly of claim 1, wherein the shield is transitionable between the locked position in which the shield is restrained within the open end of the receptacle, and the unlocked position in which the shield translates into the receiving cavity of the receptacle.

* * * * *